United States Patent
Lien (10) Patent No.: US 6,839,904 B1
(45) Date of Patent: Jan. 11, 2005

(54) HEAD-WORN SHADING VISOR

(76) Inventor: Jack Lien, 1F, No. 30, Yanji St., Kaohsiung (TW)

( * ) Notice: Subject to any disclaimer, the term of this patent is extended or adjusted under 35 U.S.C. 154(b) by 0 days.

(21) Appl. No.: 10/775,224

(22) Filed: Feb. 11, 2004

(51) Int. Cl.$^7$ ............................................. A61F 9/00
(52) U.S. Cl. ........................................ 2/12; 2/209.11
(58) Field of Search ........................... 2/12, 10, 183, 2/209.3, 195.7, 209.12, 209.11, 195.1

(56) References Cited

U.S. PATENT DOCUMENTS

| | | | |
|---|---|---|---|
| 1,213,447 A | | 1/1917 | Bacon |
| 1,401,758 A | * | 12/1921 | Carleton ............................ 2/12 |
| 1,587,681 A | * | 6/1926 | Schumacher ................. 2/175.6 |
| 1,599,576 A | * | 9/1926 | Mahony ............................. 2/12 |
| 1,640,676 A | * | 8/1927 | Shaeffer ......................... 2/174 |
| 1,718,867 A | * | 6/1929 | Mahlmann ........................ 2/12 |
| 1,732,357 A | * | 10/1929 | Davis ................................ 2/12 |
| 2,623,213 A | * | 12/1952 | Provitola et al. .......... 2/171.03 |
| 2,861,275 A | * | 11/1958 | Lougee .............................. 2/12 |
| 3,271,778 A | * | 9/1966 | Ferguson .......................... 2/12 |
| 4,694,506 A | * | 9/1987 | Perna ................................ 2/12 |
| 5,351,343 A | * | 10/1994 | Harbison ........................ 2/423 |
| 5,450,629 A | | 9/1995 | Gilstrap |
| 5,991,916 A | * | 11/1999 | Sierra ................................ 2/12 |
| 6,467,096 B1 | * | 10/2002 | Coluccio .................... 2/195.2 |
| 2003/0070203 A1 | * | 4/2003 | Lien ................................. 2/12 |

* cited by examiner

Primary Examiner—Rodney M. Lindsey
(74) Attorney, Agent, or Firm—Birch, Stewart, Kolasch & Birch, LLP (57) ABSTRACT

A head-worn shading visor includes a visor blade stitching with an annular strap. The visor blade has longitudinal grooves and transverse grooves. The visor blade has the peripheral edge stitching with the annular strap and extending upwards to form a fabric section, and extending outwards to form another annular strap to couple with an adjusting fastener which divides the another annular strap into an inner loop and an outer loop. The inner loop is abutting the visor blade and may be braced on an user's forehead for shading use. The visor blade may be folded about the longitudinal grooves and transverse grooves to become a smaller size and be coupled by the outer loop for positioning and storing.

3 Claims, 15 Drawing Sheets

HEAD-WORN SHADING VISOR

FIELD OF THE INVENTION

The present invention relates to a head-worn shading visor that is foldable in a small size to facilitate carrying and storing.

BACKGROUND OF THE INVENTION

Hat is a commonly used article for shading purpose. It generally is formed in different styles for use in different occasions. When not in use, it is difficult to store. This is a problem frequently occurred to the conventional hats.

Figure 1:
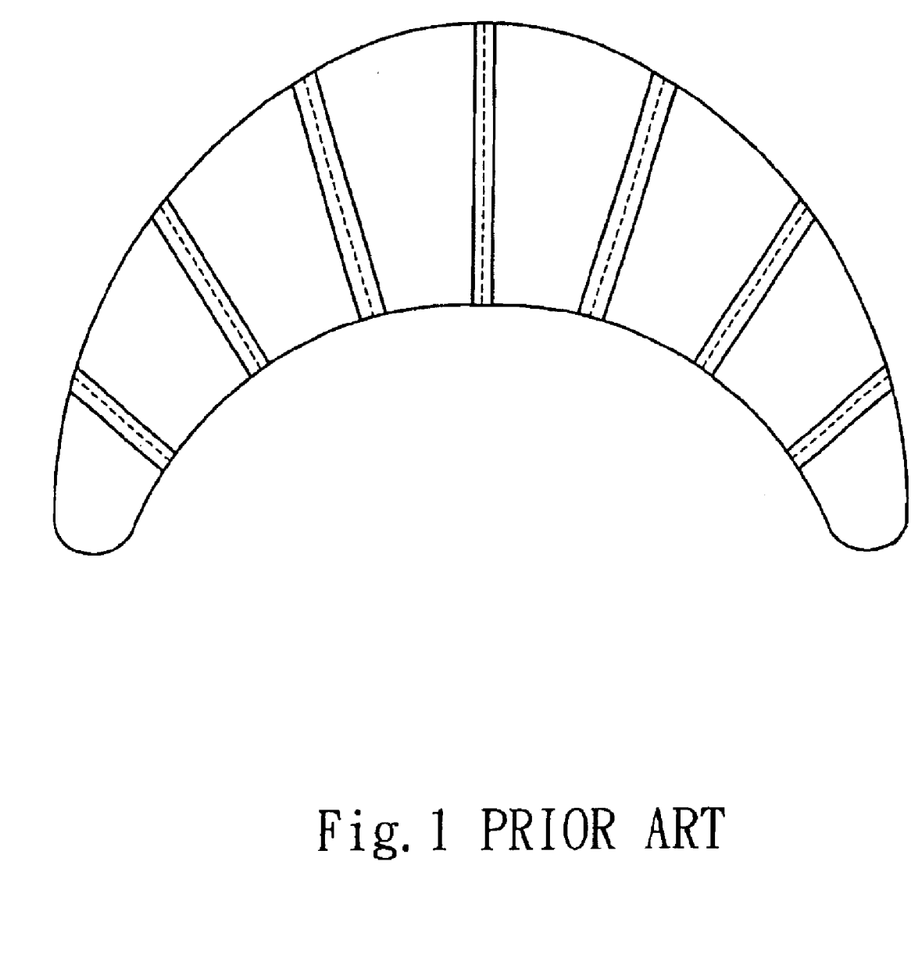
FIG. 1 is a schematic view of U.S. Pat. No. 1,213,447.
Figure 2:
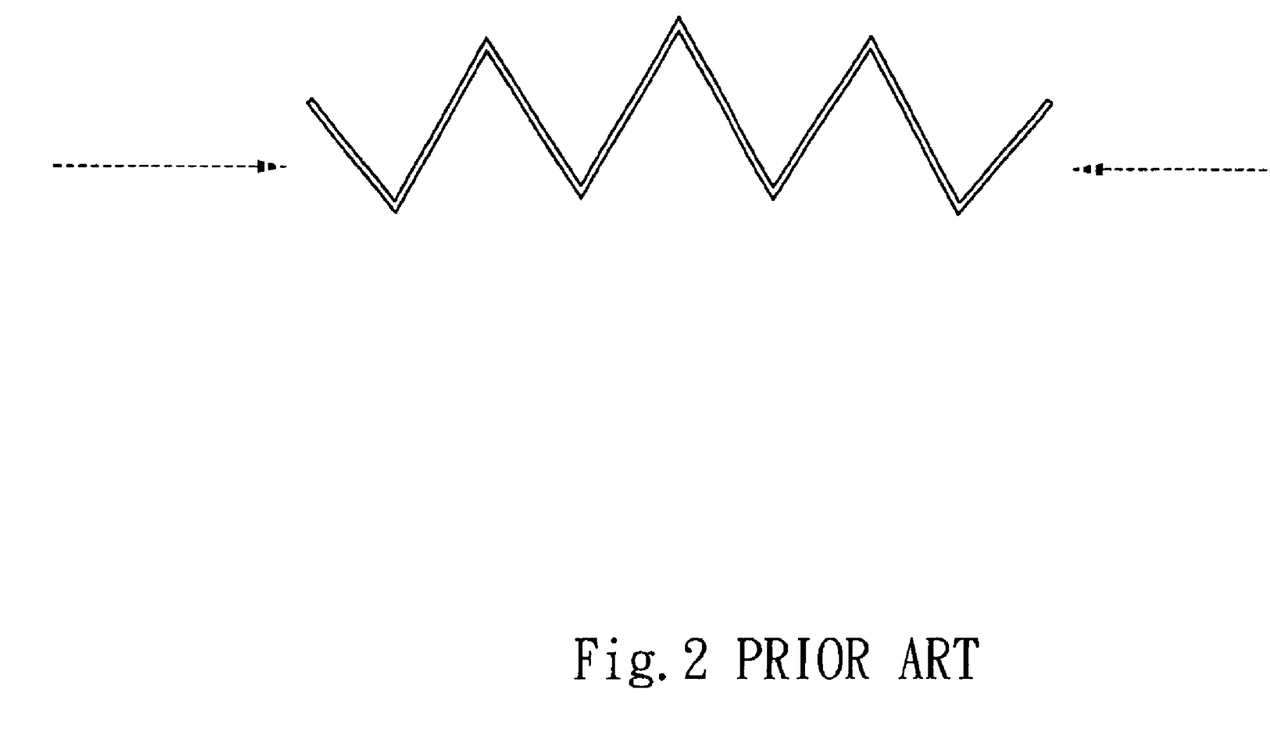
FIG. 2 is a schematic view of U.S. Pat. No. 1,213,447 in a folding condition.

In order to form the desired styles and shapes, the conventional hat usually is made from hard material. Once made, the form is fixed and not alterable. It is quite bulky and difficult to fold and store. It is inconvenient and troublesome to carry. To overcome the storing and carrying problems, many proposals have been disclosed in the prior art. U.S. Pat. Nos. 5,450,629 and 1,213,447 are two of the examples. No. 1,213,447 discloses a visor that has longitudinal fold lines to divide the visor into eight equal portions (referring to FIG. 1). It may be folded by bending inwards and outwards alternately to form a W-shape to reduce the size (referring to FIG. 2). However, such a folding structure creates some problems in use, carrying and storing, notably:

1. Folding the visor in W-shape expands the size after folding is completed. It cannot be stacked and positioned as desired.
2. The W-shaped visor has fold lines on two sides. After extended, it is difficult to form an arched shape and lacks aesthetic appealing.
3. The W-shaped visor after folding has opening ends and cannot be encased for storing.

Figure 3:
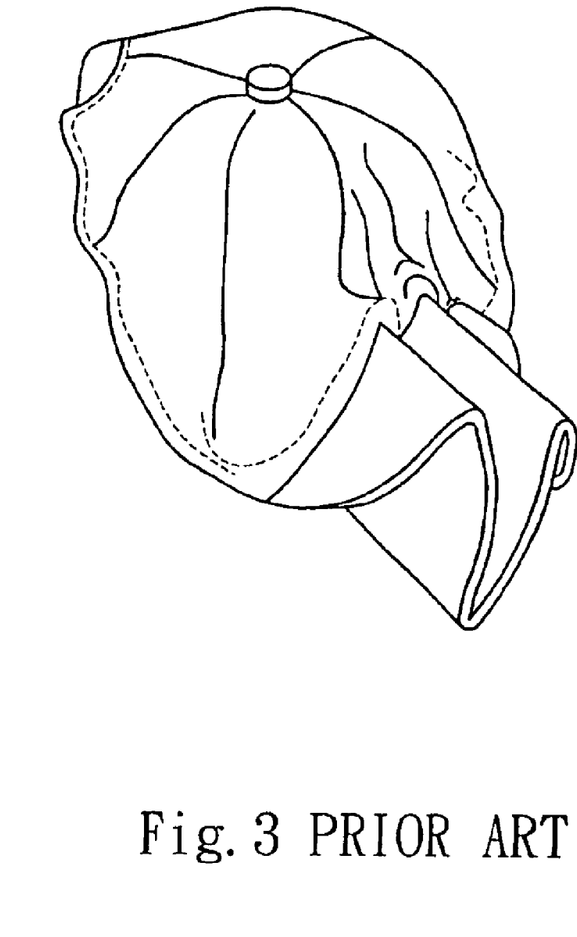
FIG. 3 is a schematic view of U.S. Pat. No. 5,450,629.

U.S. Pat. No. 5,450,629 discloses a convertible hat with a foldable visor. It has a visor divided by longitudinal fold lines into four equal portions, and also is folded in W-shape to shrink the size (referring to FIG. 3). It has an inner edge connecting to a shell to cover user's head. The shell may be used to encase the W-shaped visor. However, it also adopts the W-shape folding approach. Thus the size it can shrink is limited. And the W-shape folding also creates openings that cannot be covered or tied by the shell or strap.

SUMMARY OF THE INVENTION

The invention aims to provide a head-worn shading visor that has a visor blade with the peripheral edge coupling with an annular strap by stitching. The visor blade has a curved inner end extending upwards to form a fabric section to protect the forehead of users, and is extended outwards to form the annular strap. The annular strap is coupled with an adjusting fastener to form an inner loop and an outer loop. The inner loop is abutting the curved inner end for coupling on user's head. The adjusting fastener may be moved to adjust the size of the inner loop to suit user's head and anchor the visor blade on user's forehead for shading use. The visor has longitudinal and transverse folding grooves to fold the visor blade and the annular strap in a smaller size. Then the outer loop may be used to couple the folded visor so that it can be stored in a pocket to facilitate carrying.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 4:
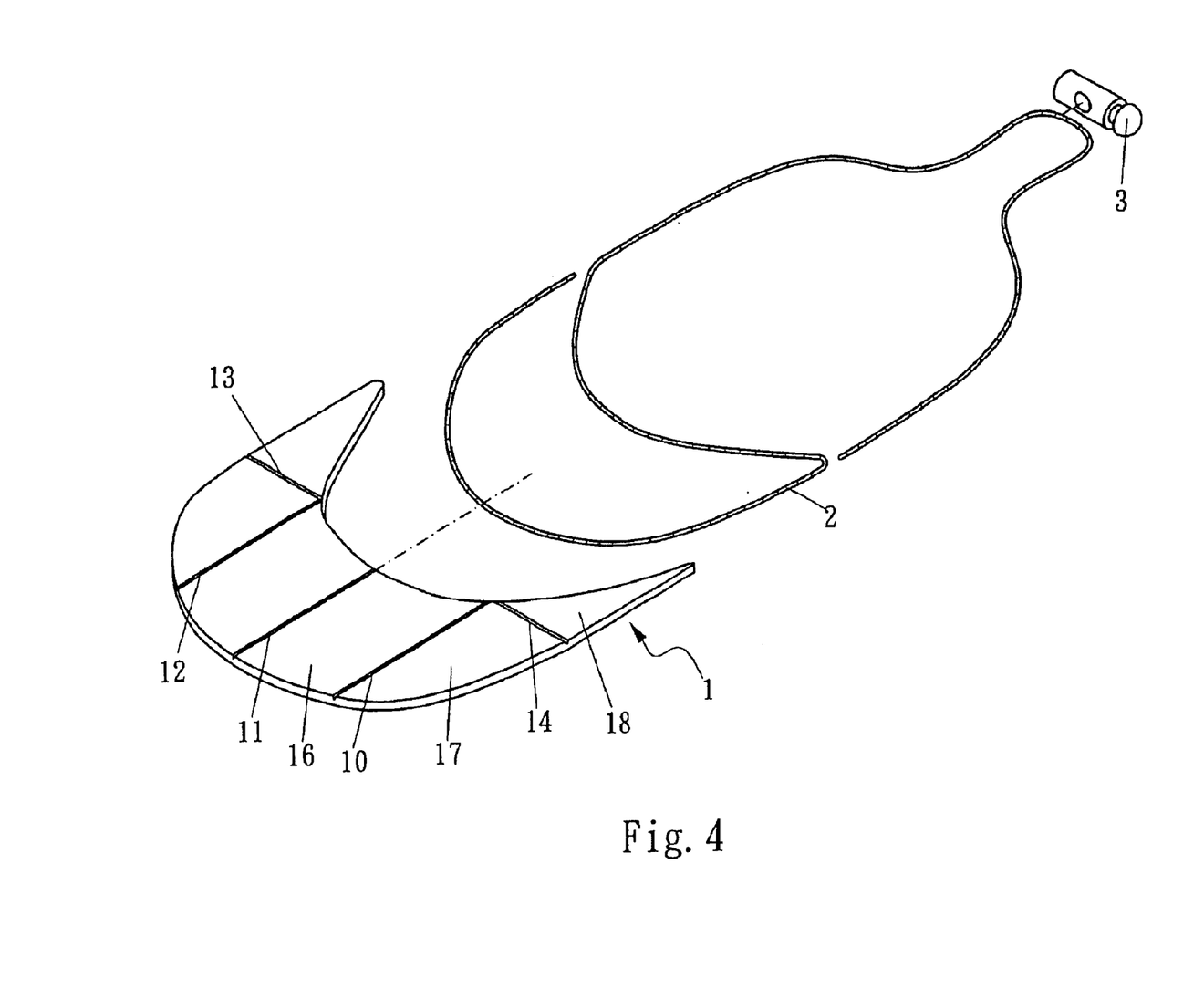
FIG. 4 is an exploded view of the present invention.
Figure 5:
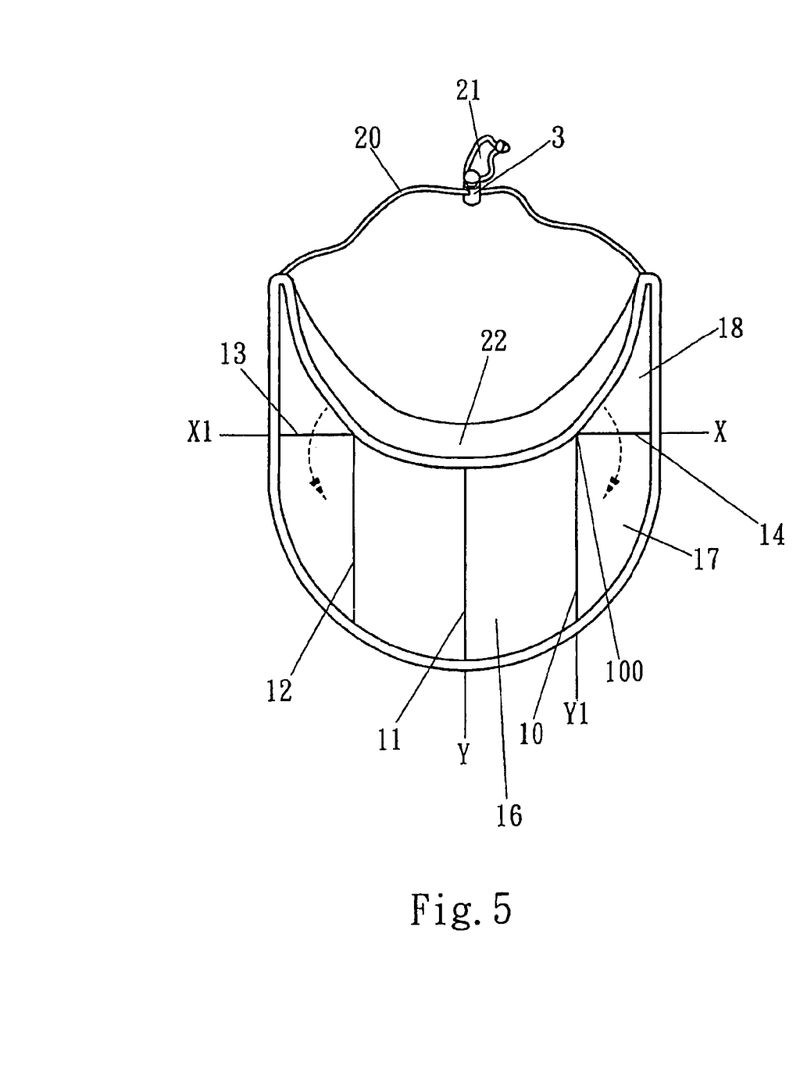
FIG. 5 is a plane view of the present invention.
Figure 6:
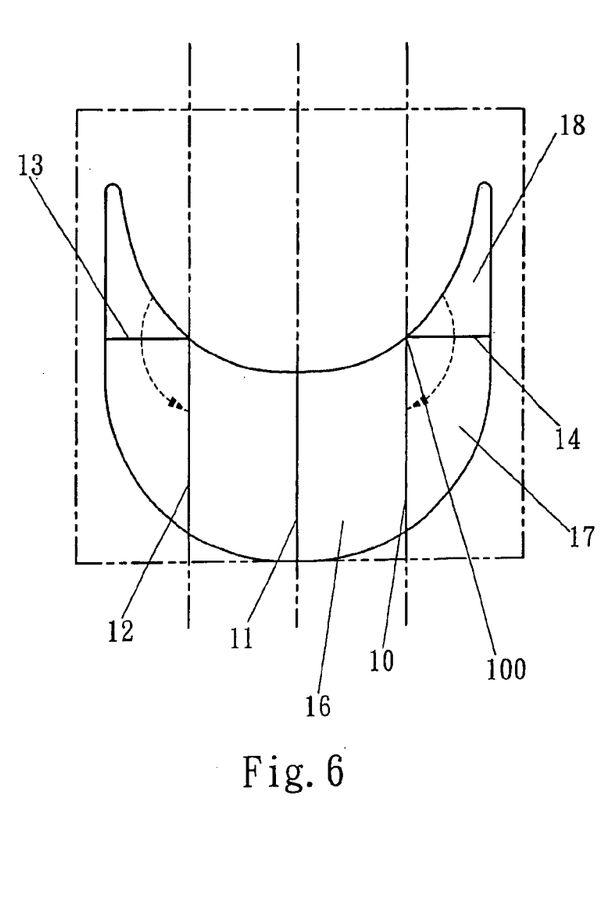
FIG. 6 is a schematic view of the visor blade of the invention.
Figure 7:
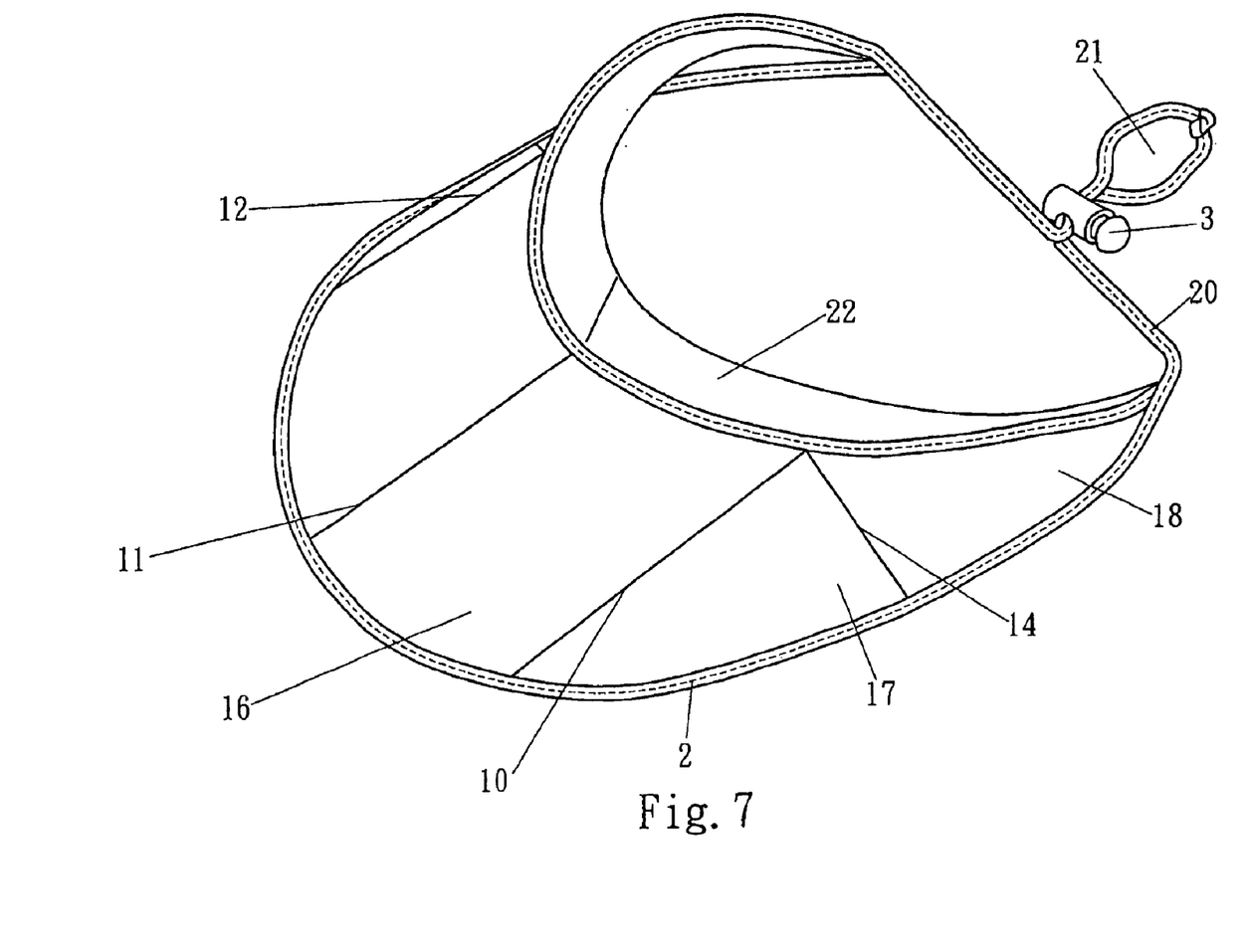
FIG. 7 is a perspective view of the invention.

Please referring to FIG. 4, the head-worn shading visor according to the invention includes a visor blade 1 which has the peripheral edge coupling with an annular strap 2 by stitching. The visor blade 1 is formed in a crescent shape, and has three longitudinal fold grooves 10, 11 and 12, and two transverse grooves 13 and 14. Referring to FIGS. 5 and 6, the longitudinal folding groove 11 is located on the center line to serve as the Y-axis. The transverse folding grooves 14 and 13 serve respectively as a X-axis and X1-axis. The X-axis and a curved inner end of the visor blade form a cross point 100 from which a vertical coordinate line Y1 is formed, and another longitudinal groove is formed thereon. The longitudinal groove 11 and the transverse groove 14 divide the visor blade 1 into a large blade 16, a medium blade 17 and a small blade 18. The annular strap 2 is stitched to the peripheral edge of visor blade 1. The curved inner end of the visor blade 1 is extended upwards to couple with a fabric section 22 to protect the forehead of users. The curved inner end further is extended outwards to form another annular strap 2 which is coupled with an adjusting fastener 3 to form an inner loop 20 and an outer loop 21 (referring to FIG. 7) for anchoring the visor blade 1.

Figure 8:
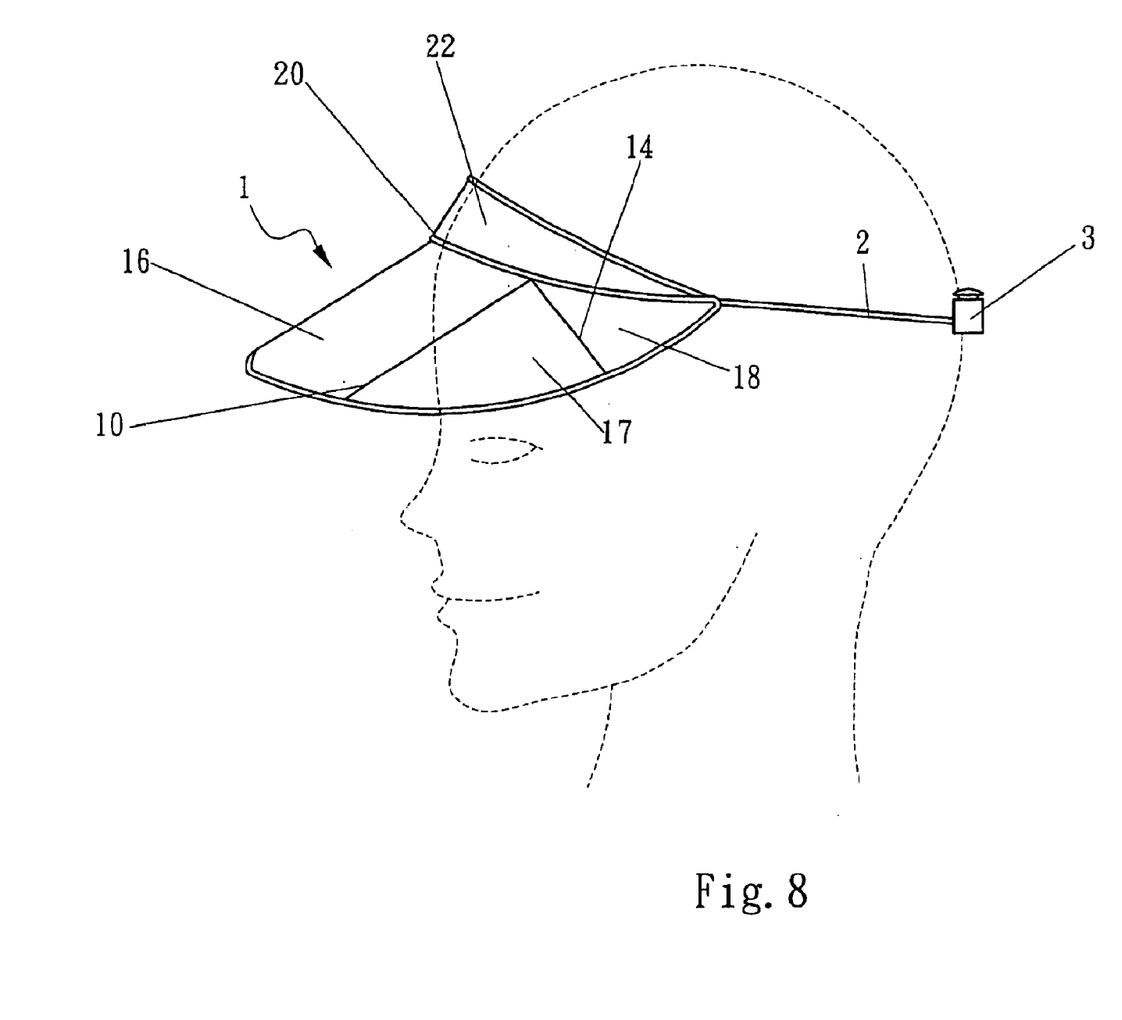
FIG. 8 is a schematic view of the invention in a use condition.

When in use for shading, the visor blade 1 is extended. The inner loop 20 abutting the curved inner end of the visor blade 1 may be worn on the head. The adjusting fastener 3 may be moved and adjusted to pull the inner loop 20 so that the visor blade 1 is braced on the forehead to provide shading effect (referring to FIG. 8).

Figure 9:
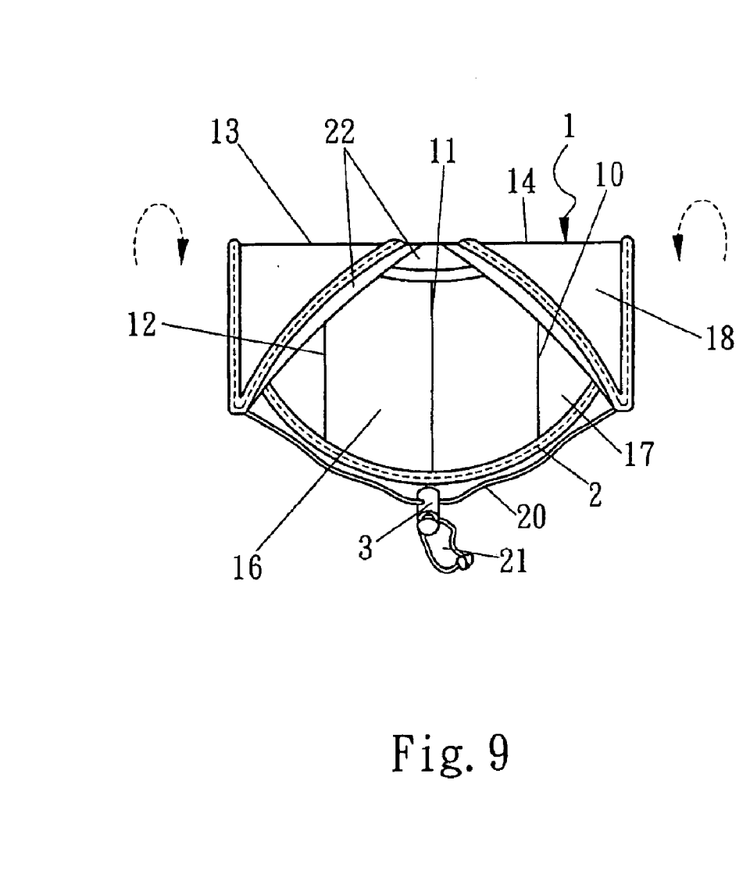
FIG. 9 is a schematic view of the invention in folding condition 1.
Figure 10:
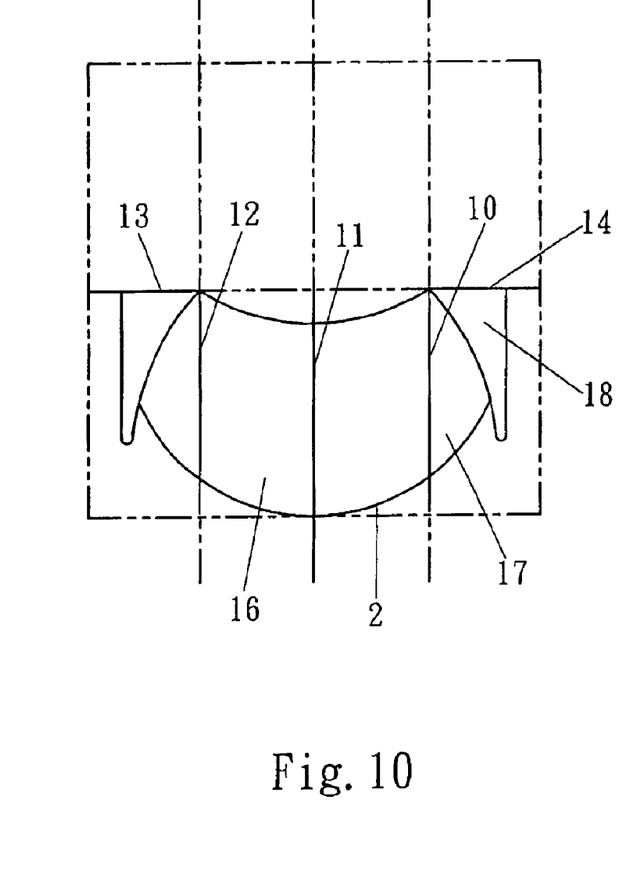
FIG. 10 is a schematic view of the invention in folding condition 2.
Figure 11:
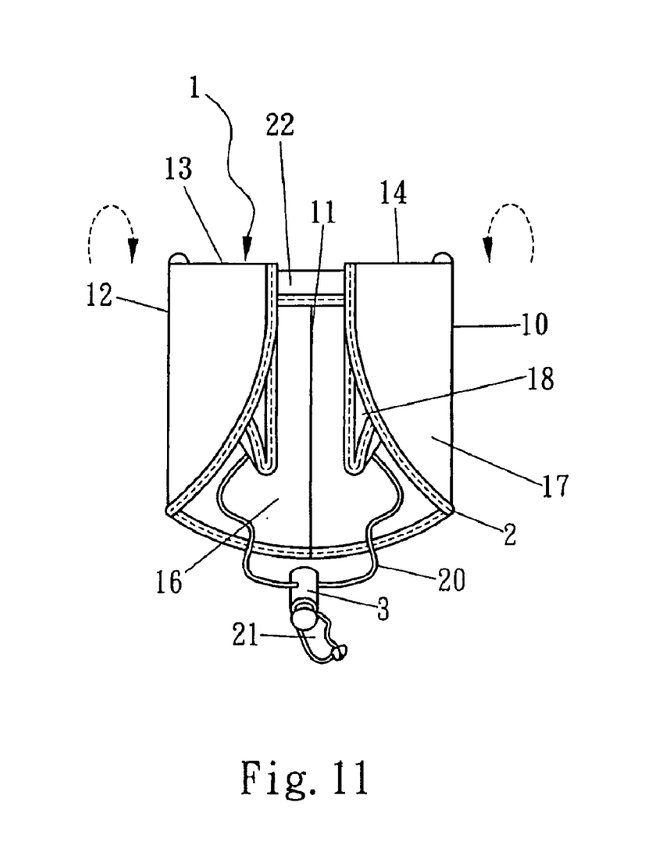
FIG. 11 is a schematic view of the invention in folding condition 3.
Figure 12:
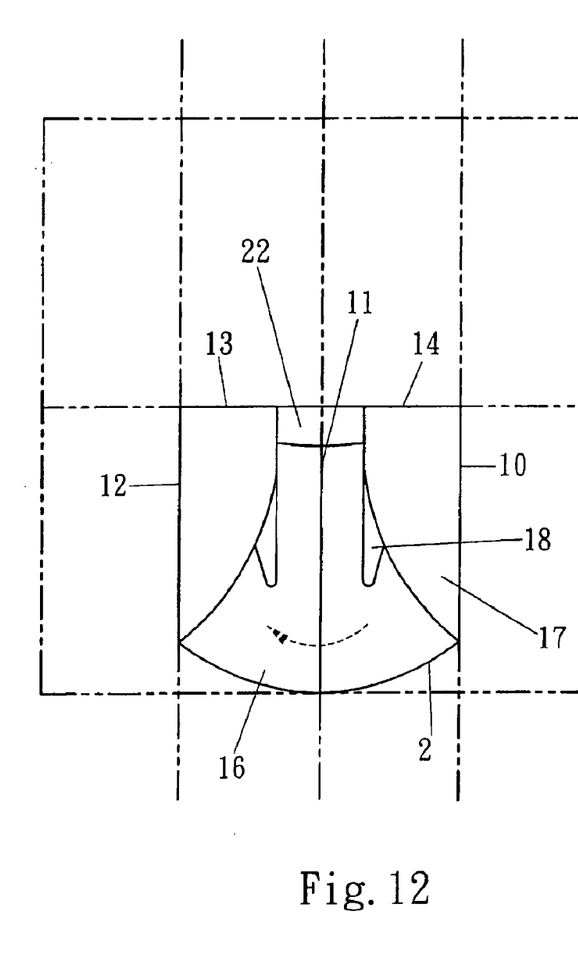
FIG. 12 is a schematic view of the invention in folding condition 4.
Figure 13:
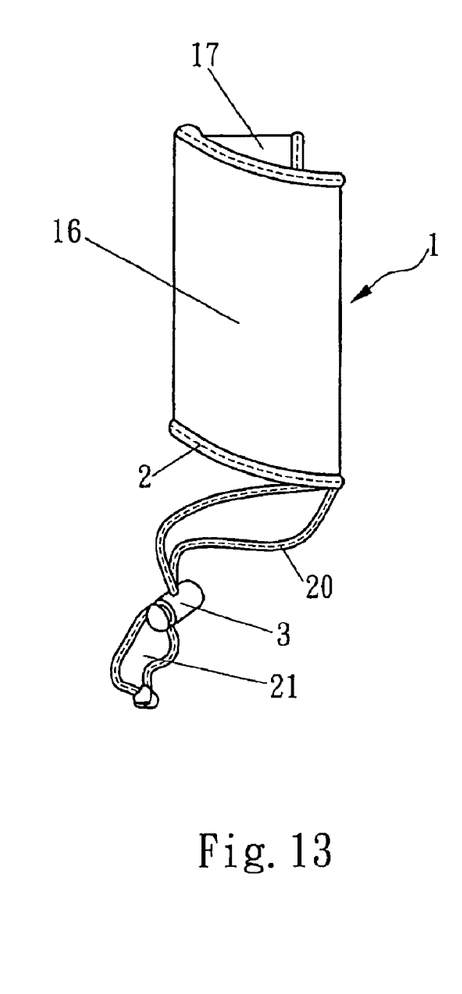
FIG. 13 is a schematic view of the invention in folding condition 5.
Figure 14:
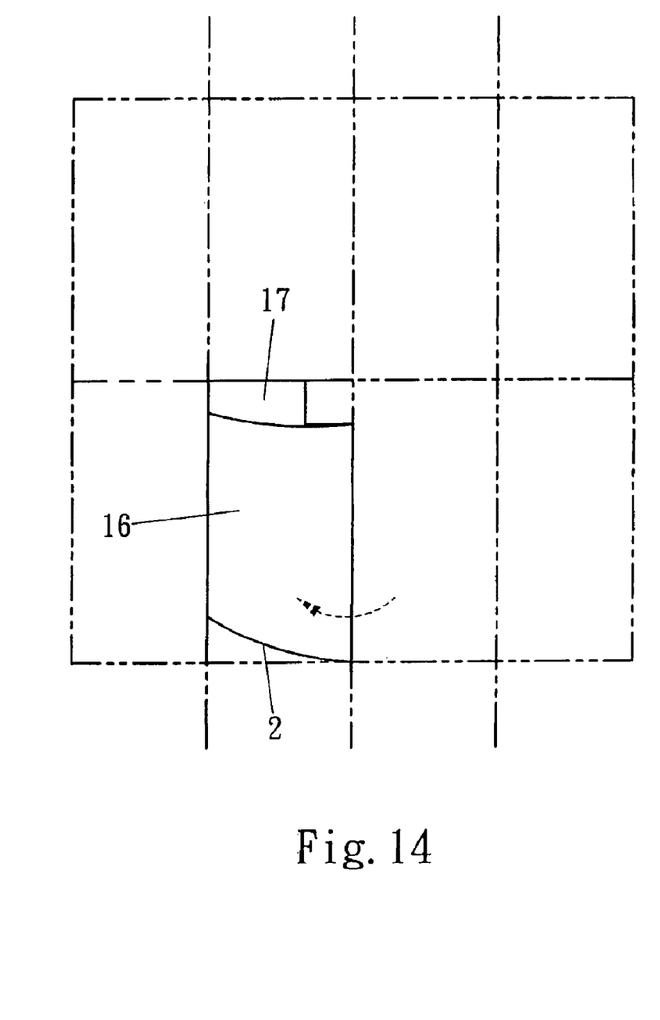
FIG. 14 is a schematic view of the invention in folding condition 6.
Figure 15:
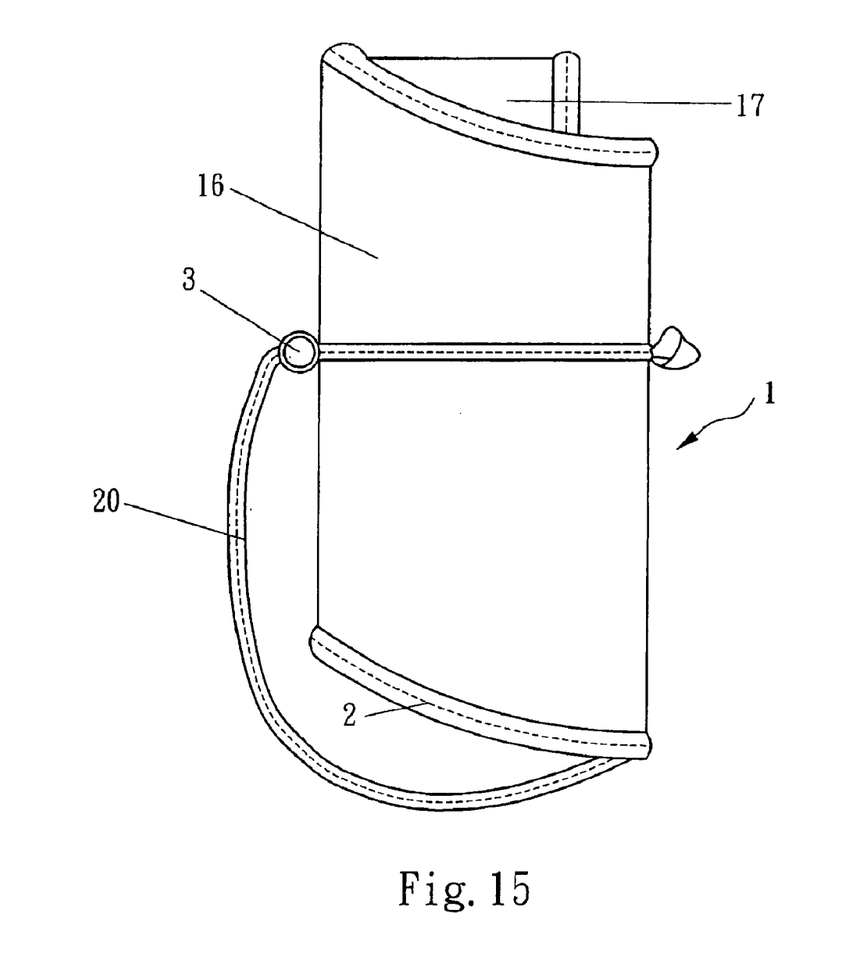
FIG. 15 is a schematic view of the invention in folding condition 7.

When not in use and folding the visor blade 1 is desired (referring to FIGS. 9 and 10), first, fold the visor blade 1 about the transverse grooves 13 and 14 at the cross point 100 of the curved inner end to fold the small blade 18 and the strap 2 and the fabric section 22 longitudinally over the medium blade 17; then fold the medium blade 17 transversely over the large blade 16 (referring to FIGS. 11 and 12); finally fold the last two large blades 16 against each other to form a shrunk and smaller body (referring to FIGS. 13 and 14). Then pull out the outer loop 21 from the adjusting fastener 3 to couple the folded body. The resulting package is small size and may be carried and stored conveniently (referring to FIG. 15).

Figure 16:
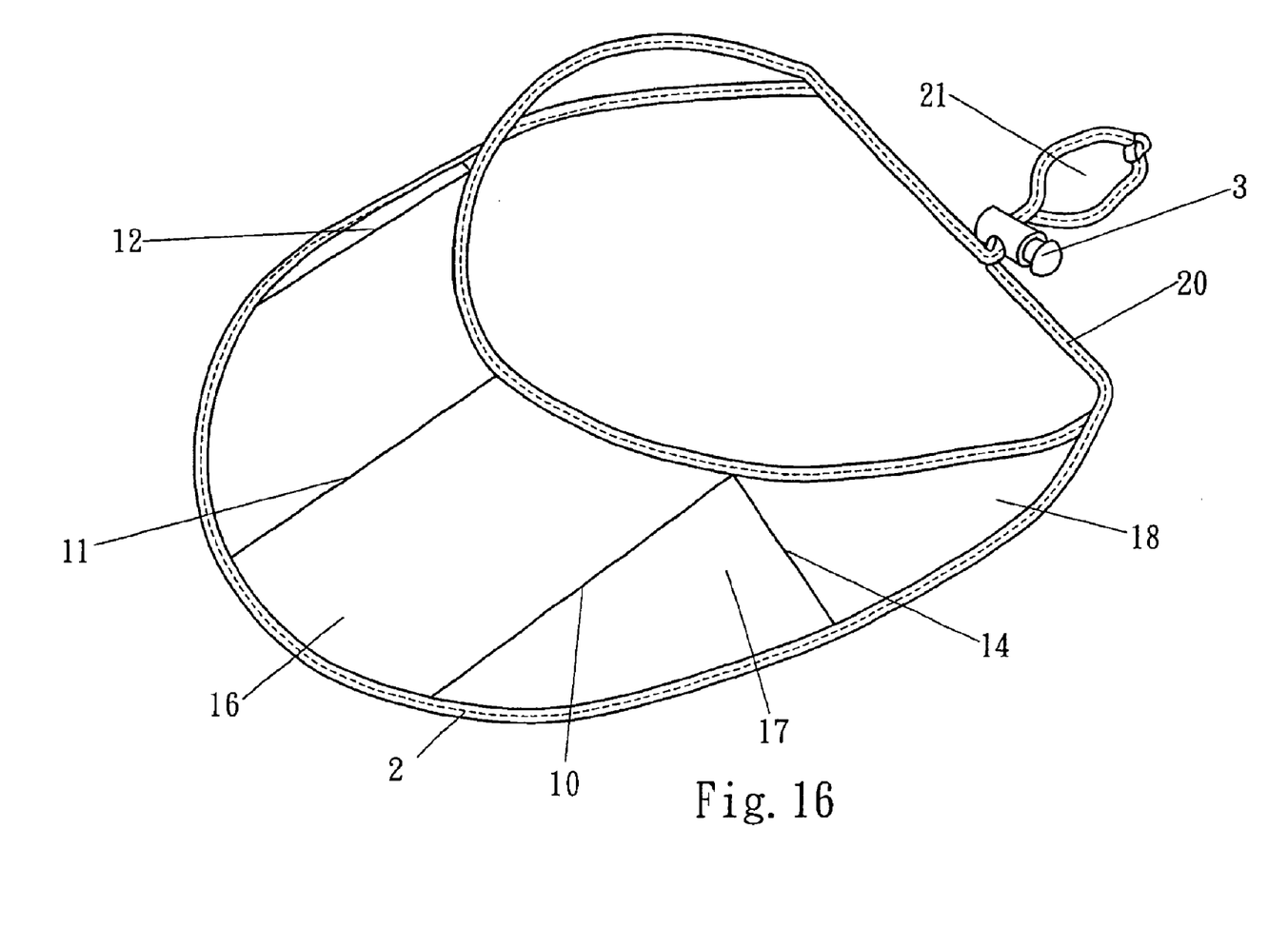
FIG. 16 is a schematic view of another embodiment of the invention.

Referring to FIG. 16, the curved inner end of the visor blade 1 may also be directly formed by stitching the annular strap 2 to form a protection rim. It may be extended to form the annular strap and coupled with the adjusting fastener to divide the annular strap into an inner loop and an outer loop to achieve shading and positioning functions.

Figure 17:
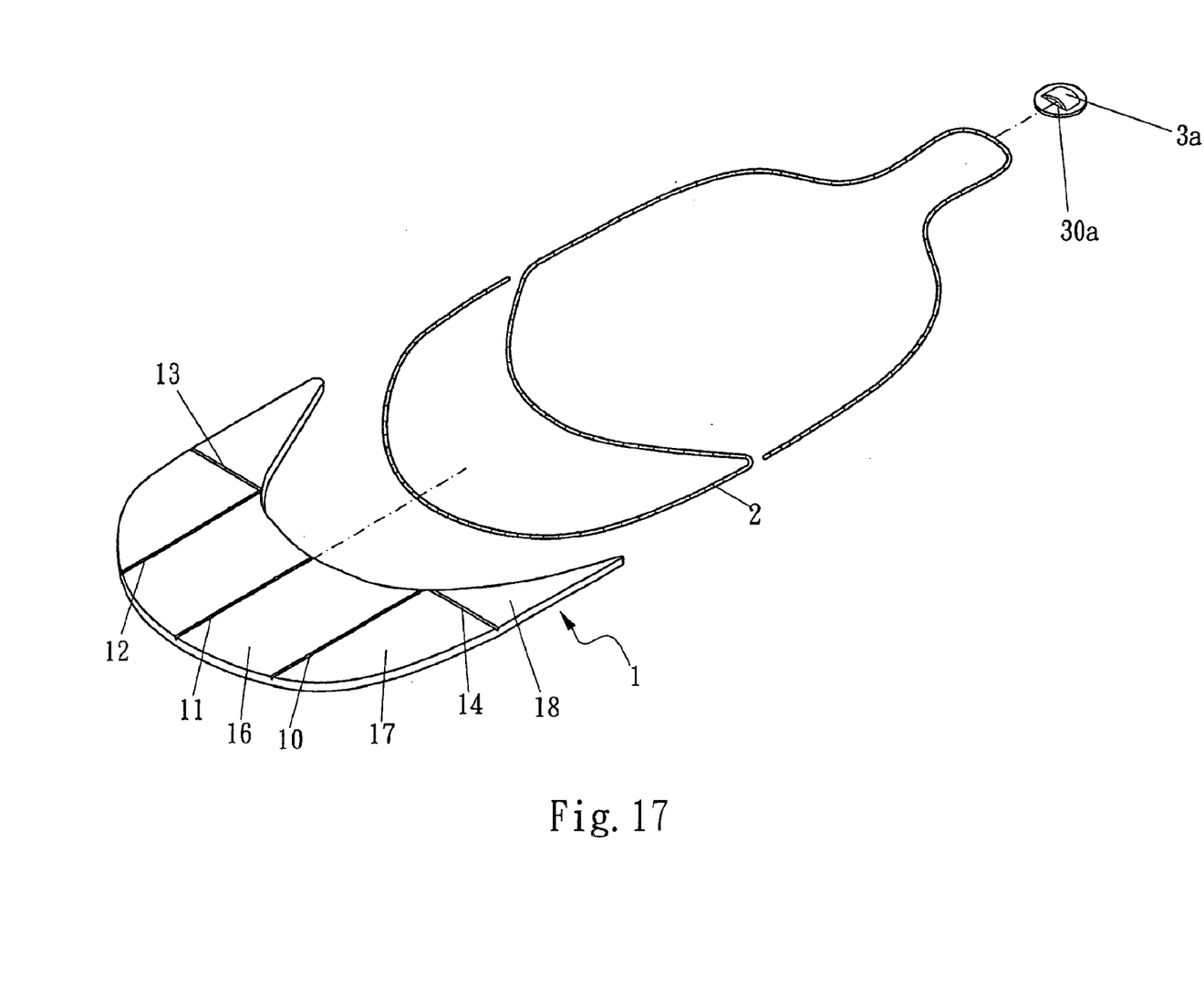
FIG. 17 is an exploded view of yet another embodiment of the invention.
Figure 18:
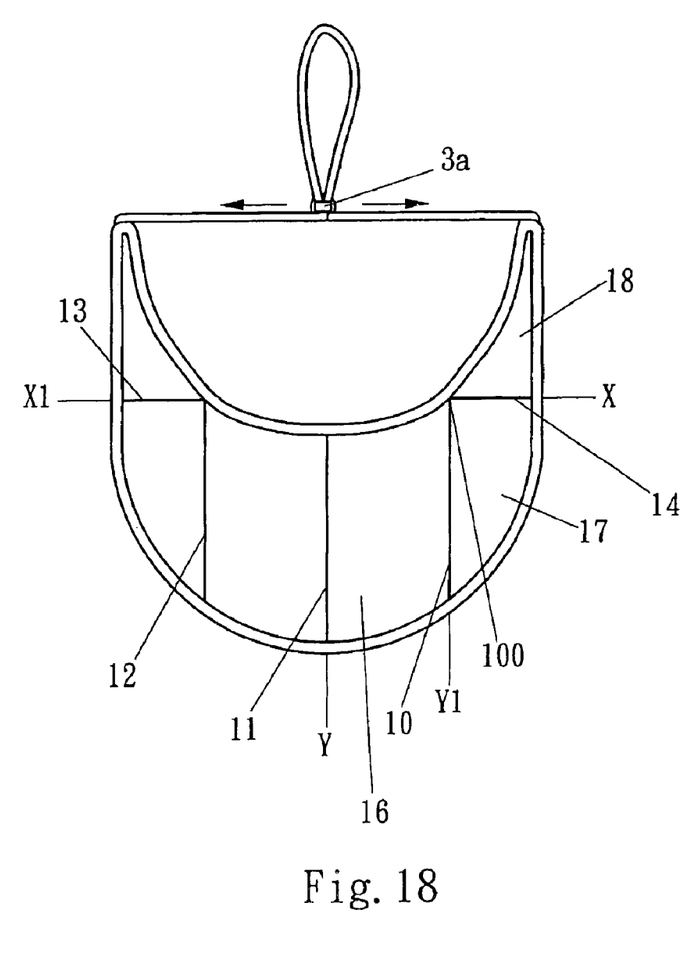
FIG. 18 is a top view of the invention according to FIG. 17.
Figure 19:
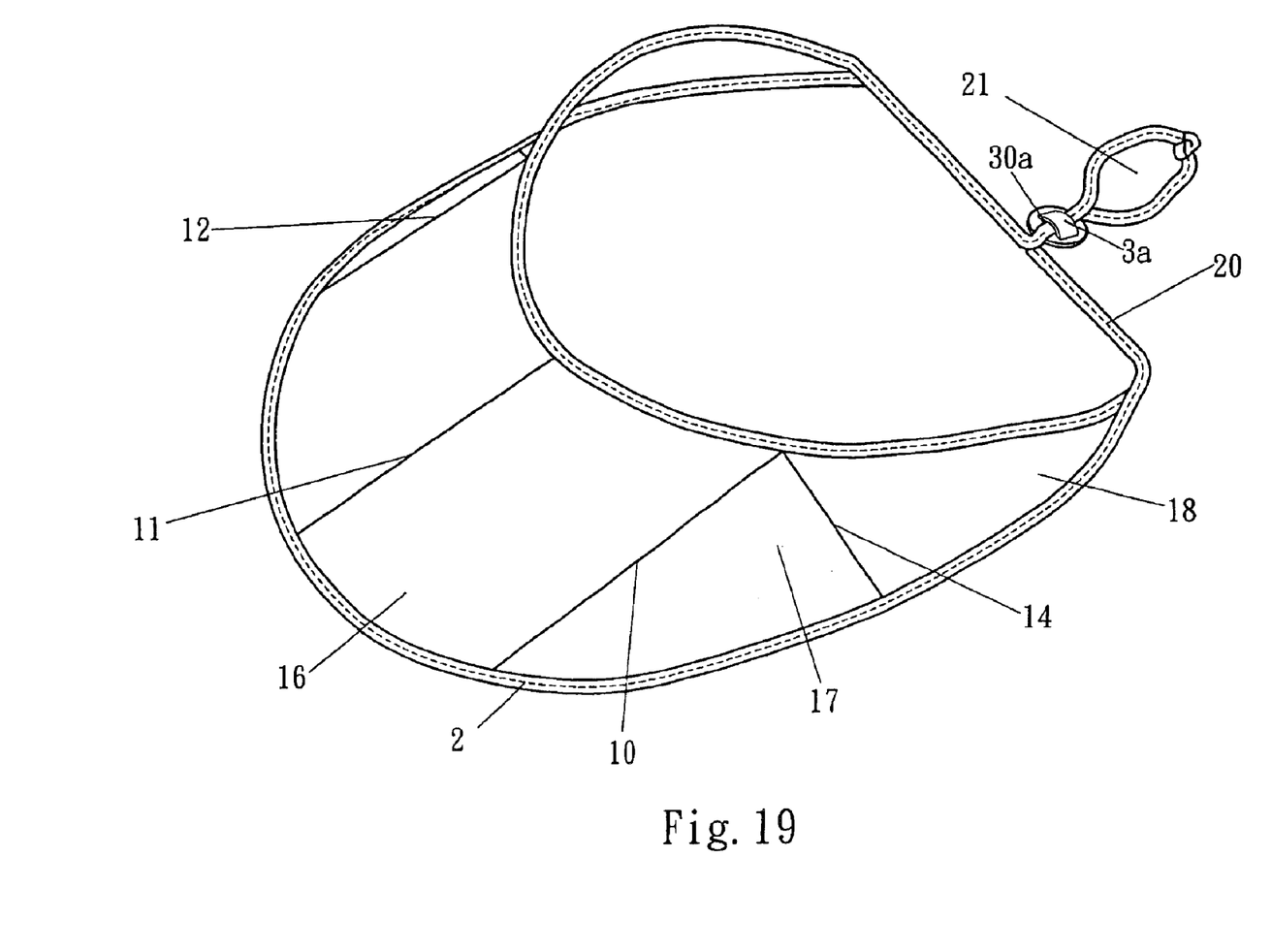
FIG. 19 is a perspective view of the invention according to FIG. 17.

Refer to FIGS. 17, 18 and 19 for yet another embodiment of the invention. The adjusting fastener 3a has a trough 30a to allow the annular strap 2 to thread there through.

What is claimed is:

1. A head-worn shading visor comprising a visor blade and a fabric section coupled together, the visor blade having a peripheral edge stitched with an annular strap and said fabric section extended upwards from said peripheral edge to form a protect for the forehead of an user and the visor blade extended outwards to from with said annular strap another annular strap to couple with an adjusting fastener which divides the another annular strap into an inner loop and an outer loop, the visor blade having longitudinal folding grooves and transverse folding grooves that are symmetrical on the left side and the right side, the longitudinal folding grooves and the transverse folding grooves dividing the visor blade into a large blade, a medium blade and a small blade;

wherein the inner loop is stitched to the visor blade and is braceable on an user's head by adjusting the adjusting fastener for shading use; the visor blade being foldable about the longitudinal folding grooves and the transverse folding grooves with the annular strap to become a smaller size to be coupled by the outer loop to facilitate positioning and carrying.

2. The head-worn shading visor of claim 1, wherein the visor blade has a curved inner end stitching with the annular strap to form a protection rim.

3. The head-worn shading visor of claim 1, wherein the adjusting fastener has a trough to allow the annular strap to thread there through.

* * * * *